United States Patent [19]
Childers et al.

[11] Patent Number: 5,866,161
[45] Date of Patent: Feb. 2, 1999

[54] HYDROCODONE THERAPY

[75] Inventors: Jerry D. Childers, Menlo Park; George V. Guittard, Cupertino; Glen E. Barclay, Sunnyvale; Anthony L. Kuczynski, Mountain View; Patrick S.-L. Wong, Palo Alto, all of Calif.

[73] Assignee: ALZA Corporation, Palo Alto, Calif.

[21] Appl. No.: 680,399

[22] Filed: Jul. 15, 1996

Related U.S. Application Data

[62] Division of Ser. No. 277,399, Sep. 16, 1994.

[51] Int. Cl.$^6$ .............................. A61K 9/22; A61K 9/24; A61K 9/30
[52] U.S. Cl. ..................... 424/465; 424/468; 424/471; 424/472; 424/473; 424/474; 424/486; 424/488
[58] Field of Search ................... 424/464, 465, 424/468, 471, 472, 473, 474, 486, 488

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,111,201 | 9/1978 | Theeuwes et al. | 128/260 |
| 4,111,202 | 9/1978 | Theeuwes | 128/260 |
| 4,327,725 | 5/1982 | Cortese et al. | 128/260 |
| 4,464,378 | 8/1984 | Hussain | 424/260 |
| 4,576,604 | 3/1986 | Guittard et al. | 604/890 |
| 4,612,008 | 9/1986 | Wong et al. | 604/892 |
| 4,844,907 | 7/1989 | Elger et al. | 424/465 |
| 4,847,077 | 7/1989 | Raghunathan | 429/79 |
| 5,021,053 | 6/1991 | Barclay et al. | 604/892 |
| 5,190,765 | 3/1993 | Jao et al. | 424/473 |

FOREIGN PATENT DOCUMENTS

| | | |
|---|---|---|
| 0220805 | 5/1987 | European Pat. Off. . |
| 0367746 | 5/1990 | European Pat. Off. . |
| 0377518 | 7/1990 | European Pat. Off. . |
| 9324154 | 12/1993 | WIPO . |

OTHER PUBLICATIONS

Hiemenz in *Polymer Chemistry,* pp. 34–43. Marcel Dekker, 1984.

Fried in *Polymer Science and Technology,* "1.3 Molecular Weight", pp. 16–18. Prentice Hall, 1995.

Mandelkern in *An Introduction to Macromolecules,* pp. 19–27. Springer–Verlag, 1983.

*Primary Examiner*—Jeffrey C. Mullis
*Attorney, Agent, or Firm*—Paul Sabatine; Susan K. Thomas; Michael J. Rafa

[57] ABSTRACT

A hydrocodone composition, a hydrocodone dosage form, and a method of administering hydrocodone are disclosed and indicated for hydrocodone therapy.

1 Claim, No Drawings

HYDROCODONE THERAPY application is a division of application Ser. No. 08/277,399, filed Sept. 16, 1994, and benefit of the filing date of said earlier filed application is claimed under 35 U.S.C. § 120.

FIELD OF THE INVENTION

This invention pertains to a novel therapeutic composition comprising hydrocodone. The invention concerns also a novel dosage form comprising hydrocodone. Additionally, the invention relates to a novel method of administering a dose of hydrocodone from a therapeutic composition, and to a novel method of administering a dose of hydrocodone from a dosage form that in both administrations are for producing antitussive and analgesic therapy.

BACKGROUND OF THE INVENTION

Hydrocodone is chemically 4,5-epoxy-3-methoxy-17-methylmorphinan-6-one. The synthesis of hydrocodone and its pharmaceutically acceptable acid addition salts are described in U.S. Pat. No. 2,71 5,629 issued to Pfister et al, and in the *Merck Index*, 11th Edition, page 757, entry 4708 (1989). Hydrocodone is a narcotic antitussive and analgesic. The mechanism of physiological and pharmacological actions of hydrocodone is believed that it acts directly by depressing the cough centers for its antitussive therapy. At antitussive doses, hydrocodone exerts also analgesic effects. Hydrocodone exhibits a complex pattern of metabolism including 0-demethylation, N-dimethylation and 6-keto reduction to the corresponding 6-β-hydroxy metabolites.

The prior art administers hydrocodone in conventional tablet and syrup forms, which forms dose-dump hydrocodone thereby providing a concentration of hydrocodone followed by an absence of hydrocodone. This pharmaceodynamic variability with its fluctuation in hydrocodone availability to hydrocodone receptor sites produces uncertainty as it is unknown if a dose of hydrocodone is present for needed therapy. The prior art is deficient in providing controlled hydrocodone therapy to a patient seeking such therapy. The pharmacological properties of hydrocodone are known in *The Pharmacological Basis of Therapy*, by Gilman and Rall, 8th Edition, pg. 497, (1990); and in *Pharmaceutical Sciences*, Remington, 17th Ed., pg. 1104, (1985).

SUMMARY OF THE INVENTION

In view of the foregoing presentation, it is immediately apparent that a present and critical need exists for an improvement in the delivery of hydrocodone for its therapeutic antitussive and analgesic effects. The need exists for providing a novel therapeutic composition comprising hydrocodone, the need exists for providing a novel dosage form comprising hydrocodone, and the need exists for providing a novel method for administering hydrocodone to a patient in need of hydrocodone therapy. It is, therefore, an object of this invention to provide a therapeutic composition comprising hydrocodone with means for enhancing the administration of hydrocodone over time. It is also an object of the invention to provide a dosage form with means for controlling the delivery of hydrocodone that overcomes fluctuation in hydrocodone therapy. It is an additional object of the invention to provide a method for administering hydrocodone for better hydrocodone therapy.

DESCRIPTION OF THE INVENTION

The drug hydrocodone, as embraced by this invention, comprises a member selected from the group consisting of hydrocodone and its pharmaceutically acceptable salts. Representative of hydrocodone pharmaceutically acceptable salts comprises a member selected from the group consisting of hydrocodone bitartrate, hydrocodone bitartrate hydrate, hydrocodone hydrochloride, hydrocodone p-toluenesulfonate, hydrocodone phosphate, hydrocodone thiosemicarbazone, hydrocodone sulfate, hydrocodone trifluoroacetate, hydrocodone, hydrocodone bitartrate, dihydrocodeinone bitartrate, hydrocodone bitartrate hemipentahydrate, pentafluoropropionate, hydrocodone p-nitrophenylhydrazone, hydrocodone o-methyloxime, hydrocodone semicarbazone, hydrocodone hydrobromide, hydrocodone mucate, hydrocodone oleate, hydrocodone phosphate dibasic, hydrocodone phosphate monobasic, hydrocodone inorganic salt, hydrocodone organic salt, hydrocodone acetate trihydrate, hydrocodone bis (heptafuorobutyrate), hydrocodone bis(methylcarbamate), hydrocodone bis(pentafluoropropionate), hydrocodone bis (pyridine carboxylate), hydrocodone bis(trifluoroacetate), hydrocodone chlorhydrate, and hydrocodone sulfate pentahydrate.

The following examples are merely illustrative of the invention, and they should not be considered as limiting the scope of the invention in any way as these examples and other equivalents thereof will become more apparent to those versed in the art.

EXAMPLE 1

A novel, therapeutic composition comprising hydrocodone, wherein the hydrocodone is a member selected from the group consisting of hydrocodone pharmaceutically acceptable base and hydrocodone pharmaceutically acceptable salt is prepared as follows: first, 3.00 g of hydrocodone bitartrate hemipentahydrate, 6.45 g of poly (ethylene oxide) and 0.50 g of hydroxypropylmethylcellulose possessing a 11,200 molecular weight are dry blended on a roll mill at 50% of the maximum speed for 5 minutes. Then, 7 ml of denatured ethyl alchohol and the dry blend are slowly mixed together with a spatula for 5 minutes. After drying, the wetted mass is passed through a 0.03331 inch (0.85 mm) screen, and it is dried overnight at room temperature. Next, 0.049 g of magnesium stearate is blended with the granulation for 2 minutes on a roll mill at 50% of maximum speed. Then, a series of extended delivery $^{11}/_{32}$ inch (8.73 mm) round tablets are prepared by compressing the composition with a 1⅛ -ton compression force. The high compression force imparts an increase in density and hardness and a decrease in fluid penetrability of the tablet thereby imparting extended delivery to the hydrocodone tablet. This hydrocodone tablet comprises 60 mg of hydrocodone bitartrate hemipentahydrate, 81.75 mg of poly(ethylene oxide), 7.5 mg of hydroxypropylmethylcellulose, and 0.75 mg of magnesium stearate.

EXAMPLE 2

The therapeutic composition manufactured by following the above example provides compositions comprising 0.5 mg to 1250 mg of a member selected from the group consisting of hydrocodone and hydrocodone pharmaceutically acceptable salt; 10 to 350 mg of a polymeric carrier for the hydrocodone selected from a poly(alkylene oxide) selected from poly(methylene oxide), poly(ethylene oxide), poly(propylene oxide), poly(isopropylene oxide) and poly (butylene oxide), and 5 to 50 mg of a hydroxyalkylcellulose or a hydroxypropylalkylcellulose as represented by a member selected from the group consisting of hydroxyethylcellulose, hydroxypropylmethylcellulose, hydroxypropylethylcellulose, hydroxypropylisopropylcellulose, hydroxypropylbutylcellulose, and hydroxypropylpentylcellulose; and 0.01 to 5 mg of a lubricant selected from the group consisting of magnesium stearate, calcium stearate, potassium oleate, sodium stearate, stearic acid, sodium palmitate, corn starch, potato starch, bentonite, citrus pulp, and stearic acid.

EXAMPLE 3

Following the procedures of Examples 1 and 2, the hydrocodone composition is encapsulated with a semipermeable polymeric composition provided with a hydrocodone-releasing orifice to provided an extended delivery dosage form.

EXAMPLE 4

A novel dosage form for delivering hydrocodone substantially free of delivery fluctuation is prepared as follows: first, 3.00 g of hydrocodone bitratrate hemipentahydrate, 6.45 g of poly(ethylene oxide), and 0.50 g of hydroxypropylmethylcellulose are dry blended on a roll mill at 50% of the maximum speed for 5 minutes. Then, 7 ml of denatured ethyl alcohol and the dry blend are slowly mixed together for 5 minutes. After drying, this wetted mass is passed through a 0.03331 inch (0.85 mm) screen, and then dried overnight at room temperature. Next, 0.049 g of magnesium stearate is blended with the granulation for 2 minutes on a roll mill at 50% of maximum speed. Then, a number of 11/32 inch (8.73 mm) tablets are compressed with 1-ton compression force. Each tablet contains 194 mg of hydrocodone drug granulation.

Next, a displacement or push composition comprising 25 to 300 mg of poly(ethylene oxide), 5 to 1 50 mg of an osmagent, 0 to 30 mg of a hydroxypropylcellulose, 0 to 10 mg of ferric oxide, 0 to 10 mg of lubricant, and 0 to 3.5 mg of antioxidant is prepared according to the examples. An embodiment of the displacement or push composition comprises 47.76 mg of poly(ethylene oxide), 22.5 mg of osmagent sodium chloride, 3.75 mg of hydroxypropylmethylcellulose of 11,200 molecular weight, 0.18 mg of ferric oxide, 0.75 mg of magnesium stearate, and 0.06 mg of butytlated hydroxytolune is prepared by the accompanying procedure.

The push granulation is fluid bed granulated at 120 kg scale on a fluid bed granulator. A binder solution is made by dissolving hydroxypropylmethylcellulose, butylated hydroxytoluene in water and ethanol. This binder solution is sprayed onto the poly(ethylene oxide), sodium chloride, hydroxypropylmethylcellulose and ferric oxide blend, while the blend is fluidized and is forming granules. After the granulation is dried, the granulation is milled in a fluid air mill. Next, a lubricant magnesium stearate is added to the dry granulation.

A semipermeable composition comprising 80:19:1, wt:wt:wt, mixture of cellulose acetate comprising an acetyl content of 39.8%, poly(vinylpyrrolidone) and triethylcitrate dissolved in an 80:20, v:v, mixture of acetone and methanol at 4% solids is sprayed around the bilayer core comprising a compressed layer of hydrocodone composition and a compressed layer of push composition to provide a compressed bilayer, to apply the semipermeable wall. Next, a 25 mil (0.64 mm) orifice is drilled into each dosage form and the dosage form dried overnight at 40° celsius. The semipermeable wall weighed 35 mg. The dosage form has a mean release rate of 6.44 mg/hr over 15 hours.

EXAMPLE 5

Following the above procedure, dosage forms are provided possessing a hydrocodone rate of release of 0.5 mg to 10 mg per hour over 20 hours.

EXAMPLE 6

The osmagent for the purpose of this invention in the hydrocodone and push compositions comprises a member selected from the osmotic solutes consisting of magnesium sulfate, sodium chloride, lithium chloride, potassium sulfate, sodium sulfate, lithium sulfate, potassium acid phosphate, mannitol, urea, inositol, magnesium succinate, tartaric acid, carbohydrates like raffinose, sucrose, glucose, lactose, fructose, sodium chloride, and fructose, and potassium chloride and dextrose.

EXAMPLE 7

The procedures above described are followed for the controlled delivery of hydrocodone at a metered rate is prepared wherein the dosage form comprises a hydrocodone layer comprising 58.08 mg of hydrocodone bitartrate hemipentahydrate, 125.06 mg of poly(ethylene oxide), 9.8 mg of hydroxypropylmethylcellulose, and 0.97 mg of magnesium stearate. A push layer comprising 47.76 mg of poly(ethylene oxide) possessing a 7,000,000 molecular weight, 22.5 mg of osmotic solute sodium chloride, 3.75 mg of hydroxypropylmethylcellulose, 0.75 mg of magnesium stearate, 0.18 mg of ferric oxide and 0.06 mg of butylated hydroxytoluene. The bilayer compositions are surrounded by a semipermeable wall comprising 25.92 mg of cellulose acetate comprising 39.8% acetyl content, 6.15 mg of poly(vinylpyrrolidone) and 0.324 mg of plasticizer triethyl citrate. The dosage forms comprise a 25 mil (0.64 mm) orifice and exhibits a mean release rate of 5.105 mg/hr of hydrocodone over a sustained period of therapy over 16 hours.

EXAMPLE 8

The procedures of the above examples are followed to produce a hydrocodone composition comprising 60.00 mg of hydrocodone bitartrate hemipentahydrate, 81.75 mg of poly(ethylene oxide) molecular weight, 7.50 mg of hydroxypropylmethylcellulose of, and 0.75 mg of magnesium stearate. The semipermeable wall that surrounded the hydrocodone comprises 75:24:1, wt:wt:wt, mixture of cellulose acetate with an acetyl content of 39.8%, poly(vinylpyrrolidone) and triethyl citrate. The semipermeable composition is dissolved in a 80:20, v:v, mixture of acetone and methanol at 4% solids. The semipermeable wall weighed 43.4 mg.

EXAMPLE 9

Representative of antioxidants for providing the dosage forms of this invention comprise a member selected from the group consisting of d-alpha tocopherol, dl-alpha tocopherol, d-alpha-tocopherol acetate, dl-alpha-tocopherol, ascorbyl palmitate, ascorbic acid, butylated hydroxyanisole, butylated hydroxytoluene, and propyl gallate.

EXAMPLES 10–11

The procedure of the above examples is followed except in these examples there is provided in one manufacture a hydrocodone composition comprising a poly(ethylene oxide), and in another manufacture the hydrocodone composition comprises the hydrocodone composition comprising a poly(ethylene oxide).

EXAMPLE 12

The wall provided by the above examples are semipermeable possessing a permeability to aqueous including biological fluids and impermeable to hydrocodone. The semipermeable walls comprise 15 mg to 200 mg of a cellulose polymer selected from the group consisting of a cellulose ester, cellulose diester, cellulose triester, cellulose ether, cellulose ester-ether, cellulose acylate, cellulose diacylate, cellulose triacylate, cellulose acetate, cellulose diacetate, and cellulose triacetate; the wall comprises 0 to 5 mg of a plasticizer represented by a member selected from the group consisting of trimethyl citrate, triethyl citrate, tributyl citrate, acetyltributyl citrate, acetyl tri-2-ethyl citrate, tributyl phosphate, triethyl phosphate, triphenyl citrate, tricyclohexyl citrate, and tricresyl citrate; the semipermeable wall comprises 2 mg to 50 mg of a poly(vinyl) polymer as represented by poly(vinyl pyrrolidone), copolymer of poly(vinyl-pyrrolidone and (vinyl acetate), copolymer of poly(vinyl pyrrolidone and vinyl alcohol), copolymer of poly(vinyl pyrrolidone and vinyl chloride), copolymer of poly(vinyl pyrrolidone and vinyl fluoride), copolymer of poly(vinyl pyrrolidone and vinyl butyrate), copolymer of poly(vinyl pyrrolidone and vinyl laurate),and copolymer of poly (vinyl pyrrolidone and vinyl stearate).

Exemplary solvents used for the present purpose comprise inorganic and organic solvents that do not adversely harm the materials and the final wall or the final compositions in the dosage form. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monethyl acetate, methylene dichloride, ethylene dichloride, propylene dichloride, carbon tetrachloride, chloroform, nitroethane, nitropropane, tetrachloroethane, ethyl ether, isopropyl ether, cyclo-hexane, cyclo-octane, benzene, toluene, naphtha, 1, 4 -dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

Exit means, as used in the above examples for the dosage forms as used by this invention comprise means and methods suitable for the metered release of beneficial drug hydrocodone from the dosage form. The exit means comprises at least one passageway, orifice, or the like, through the wall for communicating with hydrocodone the dosage form. The expression, "at least one passageway", comprises aperture, orifice, bore, pore, porous element through which the hydrocodone can migrate, hollow fiber, capillary tube, porous overlay, porous insert, and the like. The expression also includes a material that erodes or is leached from the wall in the fluid environment of use to produce least one passageway in the dosage form. Representative materials suitable for forming at least one passageway, or a multiplicity of passageways, include an erodible poly(glycolic) acid, or poly(lactic) acid member in the wall, a gelatinous filament, poly(vinyl alcohol), leachable materials such as fluid removable s pore forming polysaccharides, salts, oxides, or the like. A passageway or a plurality of passageways can be formed by leaching a material such as sorbitol, lactose, fructose and the like from the wall. The passageway can have any shape such as round, triangular, square, elliptical, and the like, for assisting in the metered release of hydrocodone from the dosage form. The dosage form can be constructed with one or more passageways in spaced apart relations, or more than one passageway on a single surface of a dosage form. Passageways and equipment for forming passageways are disclosed in U.S. Pat. Nos. 3,845,770, 3,916,899; 4,063,064; and 4,088,864. Passageways is of govern size formed by leaching are disclosed in U.S. Pat. Nos. 4,200,098 and 4,285,987.

EXAMPLE 13

A dosage form adapted, designed and shaped for the oral delivery of hydrocodone to a patient in need of hydrocodone therapy is manufactured as follows: first, 8.00 g of hydrocodone bitartrate hemipentahydrate, 5.50 g of sorbitol, 4.20 g of sodium carboxymethylcellulose and 1.00 g of hydroxypropylmethylcellulose are screened separately through a 0.01 65 inch (0.42 mm) 40 mesh screen. Next, the screened materials are blended on a three roll mill for 20 minutes to produce a homogenous blend. Then, a granulation is prepared by dissolving 1.20 g of poly(vinyl pyrrolidone) and 10 ml of denatured ethyl alcohol with constant stirring to provide a granulation fluid. Then, to all the ingredients on the milling machine, the granulation fluid is slowly added, and all the ingredients blended slowly for 5 minutes, to yield a wet granulation. The wetted mass is then passed through a 0.03331 inch (0.85 mm) 20 mesh screen and air dried at room temperature in a light current of moving air. After drying, the granulation is blended for an additional 2 minutes on a standard roll mill at 50% of its maximum speed. Then, 5/16 inch (7.94 mm) round tablets, each comprising 150 mg of the hydrocodone composition are compressed on a Carver® press under a ¼ -ton compression force to provide the first layer of a bilayer core. The hydrocodone composition comprises 60.00 mg of hydrocodone bitartrate hemipentahydrate, 41.25 mg of sorbitol, 31.50 mg of sodium carboxymethylcellulose 9.00 mg of poly(vinylpyrrolidone), 7.50 mg of hydroxypropylmethylcellulose and 0.75 mg of magnesium stearate.

A composition for providing a push layer of a bilayer core arrangement is prepared comprising 44.06 mg of sodium carboxymethylcellulose, 22.50 mg of sodium chloride, 3.75 mg of hydroxypropylmethylcellulose, 0.75 mg of ferric oxide and 0.19 mg of magnesium stearate are used for preparing the push composition. A push granulation is prepared on a fluid bed granulator. A binder solution is made by dissolving hydroxypropylmethylcellulose in water. The binder solution is sprayed on the sodium carboxymethylcellulose 7H, the sodium chloride, hydroxypropylmethylcellulose and ferric oxide push-forming blend while the blend is fluidized and the granules are formed in the granulator. After the granulation is dried overnight at room temperature, the blend is remilled in a fluid air mill, and magnesium stearate is added to the mill.

The push-forming coposition is compressed into a 5/16 inch (7.94 mm) round layer with each layer comprising 75 mg of the push composition using a Carver® press under a compression force of 1⅛ ton to provide the second layer of the bilayer core. The hydrocodone layer and the push layer are coated with a semipermeable wall-forming composition in a 11 13/16 inch (30 cm) coater. The semipermeable wall-forming composition comprises a 75:24:1, wt:wt:wt, mixture of cellulose acetate having a 39.8% acetyl content, poly(vinylpyrrolidone), and triethyl citrate. The wall-forming components are dissolved in a 80:20, wt:wt, mixture of acetone and methanol at 4% solids. The average wet semipermeable wall weighted 36.8 mg. A single 25 mil (0.64 mm) passageway is drilled into each dosage form, and then the dosage forms are dried overnight at 40° celsius. The dosage form exhibited a mean release rate of 8.212 mg/hr over an extended 12 hours of therapy.

EXAMPLE 14

The procedure of the above example is followed for manufacturing a dosage form, characterized by a hydrocodone layer consisting of 0.5 to 1250 mg of hydrocodone, 10 to 50 mg of sorbitol, 10 to 50 mg of alkali carboxymethylcellulose, 5 to 50 mg of hydroxypropylalkylcellulose of, 0 to 20 mg of poly(vinyl-pyrrolidone) of, and 0.01 to 5 mg of a lubricant; and a push composition comprising 10 to 60 mg of alkali carboxymethylcellulose, which is a higher molecular weight then the molecular weight of the alkali carboxymethylcellulose present in the hydrocodone composition, 5 to 75 mg of osmagent, 1 to 30 mg of hydroxypropylmethylcellulose, 0 to 10 mg of ferric oxide, and 0 to 10 mg of lubricant.

DISCLOSURE FOR USING THE INVENTION

The invention concerns also a method for administering 0.5 mg to 1250 mg of hydrocodone to a patient in need of hydrocodone therapy. The method, in one administration comprises admitting orally into the patient 0.5 mg to 1250 mg of a hydrocodone selected from the group consisting of hydrocodone, and hydrocodone pharmaceutically acceptable salt, which is administered from a therapeutic composition comprising 0.5 mg to 1250 mg of hydrocodone, 10 mg to 350 mg of a poly(alkylene oxide), 5 mg to 50 mg of a hydroxyalkylcellulose and 0.01 mg to 5 mg of a lubricant, which composition provides hydrocodone therapy over an extended period of time.

The invention concerns further a method for administering 0.5 mg to 1250 mg of hydrocodone by admitting orally 0.5 mg to 1250 mg of hydrocodone to a patient administered from a dosage form comprising a semipermeable wall permeable to aqueous and biological fluid and impermeable to the passage of hydrocodone, which semipermeable wall surrounds an internal compartment comprises a hydrocodone composition and a push composition. The hydrocodone composition consists of the composition above, and the push composition comprises 25 to 300 mg of a poly (alkylene oxide), 5 mg to 150 mg of an osmagent, 1 to 30 mg of a hydroxypropylmethylcellulose, 0 to 10 mg of ferric oxide, 0 to 10 mg of lubricant and 0 to 3.5 mg of an antioxidant; and an exit means in the semipermeable wall for delivering the hydrocodone from the dosage form. The dosage form delivers the hydrocodone by imbibing fluid through the semipermeable wall into the dosage form causing the hydrocodone composition to change from a resting state to a dispensable state, and simultaneously causing the push composition to imbibe fluid, expand and push the hydrocodone composition through the exit, whereby through the combined operations of the dosage form the hydrocodone is delivered at a therapeutically effective dose at a controlled over an extended period of time.

Inasmuch as the foregoing specification comprises numerous embodiments, it is understood that variations and modifications can be made herein, in accordance with the principles disclosed, without departing from the invention.

We claim:

1. A method for administering hydrocodone to a patient in need of hydrocodone therapy, which method comprises orally admitting into the gastrointestinal tract of the patient a sustained delivery bilayer comprising a hydrocodone layer comprising up to 1250 mg of hydrocodone, 10 mg to 350 mg of poly(alkylene oxide), 5 to 50 mg of a hydroxyalkylcellulose, and 0.01 to 5 mg of a lubricant; and a push layer comprising 25 mg to 300 mg of a poly(alkylene oxide), 5 to 150 mg of an osmagent, and 1 to 30 mg of a hydroxypropylalkylcellulose, which bilayer through the combined operation of the bilayer imbibes fluid and releases hydrocodone, thereby delivers the hydrocodone at a controlled rate of 0.5 mg to 10 mg per hour over a period of 30 hours to the gastrointestinal tract of the patient in need of hydrocodone therapy.

* * * * *